(12) United States Patent
Münch et al.

(10) Patent No.: US 6,283,932 B1
(45) Date of Patent: Sep. 4, 2001

(54) ORTHOPEDIC DEVICE

(76) Inventors: Thomas Münch, Neuhausweg 88, D-47167 Duisburg; Meinald Settner, An der Dellen 35a, D-40885 Ratingen, both of (DE)

( * ) Notice: Subject to any disclaimer, the term of this patent is extended or adjusted under 35 U.S.C. 154(b) by 0 days.

(21) Appl. No.: 09/307,053

(22) Filed: May 7, 1999

(30) Foreign Application Priority Data

May 8, 1998 (DE) .......................................... 298 08 341 U

(51) Int. Cl.$^7$ .............................. A61F 5/00; A61F 13/00; A61F 5/37
(52) U.S. Cl. ................................ 602/23; 602/27; 602/66; 602/6; 128/882
(58) Field of Search .................................. 602/5, 23, 27, 602/60–63, 65, 66; 36/89, 91, 145, 159, 155, 140; 128/882, 845, 846

(56) References Cited

U.S. PATENT DOCUMENTS

| | | | | |
|---|---|---|---|---|
| 1,417,170 | * | 5/1922 | Hosmer | 36/140 |
| 1,737,897 | * | 12/1929 | Skoglund | 602/65 X |
| 5,070,867 | * | 12/1991 | March | 36/145 |
| 5,799,659 | * | 9/1998 | Stano | 126/882 |
| 5,833,639 | * | 11/1998 | Nunes et al. | 602/23 |
| 5,980,475 | * | 11/1999 | Gibbons | 602/11 |
| 6,090,059 | * | 7/2000 | Wasserman | 602/27 |

FOREIGN PATENT DOCUMENTS

| | | | |
|---|---|---|---|
| 94 20 046.7 | | 4/1995 | (DE) . |
| 539243 | * | 9/1941 | (GB) ..................................... 602/65 |

* cited by examiner

*Primary Examiner*—Denise Pothier
(74) *Attorney, Agent, or Firm*—Collard & Roe, P.C.

(57) ABSTRACT

An orthopedic device comprises a shaft capable of at least partially encircling at least a lower part of a leg, a foot part, a cup-shaped heel part connecting the foot part to the shaft, a continuous bearing surface arranged between the front end of the foot part and the heel part, the bearing surface constituting a lower closure of the orthopedic device and having a side facing the interior of the orthopedic device, which is flat and symmetrical with respect to a central longitudinal axis, and an arch support affixable to said bearing surface side. A portion of the arch support running along an outside of a foot capable of being supported by the arch support extends substantially horizontally, and a portion of the arch support running along an inside of the foot has a shape of a rising arc, a flank of the arc near the heel rising substantially perpendicularly from the bearing surface to an apex and extending from the apex to the foot part.

11 Claims, 4 Drawing Sheets

ORTHOPEDIC DEVICE

BACKGROUND OF THE INVENTION

1. Field of the Invention

The present invention relates to an orthopedic device, such as a heel relief device, comprising a shaft capable of at least partially encircling at least a lower part of a leg, a foot part having a front end, a saucer-shaped heel part connecting the foot part to the shaft, and a continuous bearing surface arranged between the front end of the foot part and the heel part, the bearing surface constituting a lower closure of the orthopedic device.

2. Description of the Prior Art

Orthopedic devices of this type are used, for example, after bone fractures in the heel or rear portion of a foot, the main purpose being to relieve the heel bone from pressure while the fracture heals and to position it so that it floats freely without contact. Such an orthopedic device is disclosed, for instance, in German utility model No. 94 20 046.7, which is not a printed publication under U.S. patent law.

These known orthopedic devices permit a dorsal contact of the shaft with the calf and a support of the arch, which on the one hand assures a free-floating positioning of the heel bone and, on the other hand, enables almost normal walking in a manner reminiscent of modern ski boots. The heel part of such an orthopedic device extends rearwardly, and its saucer shape provides a rounded rear edge therefor. In this way, the forces generated when the foot is put down are transmitted during the motion from the heel part to the shaft in contact with the calf. As the foot motion proceeds, the freely floating heel bone is not subjected to any load because the ensuing forces are transmitted to the arch of the foot.

A tight tying and constriction of the lower leg muscles is not necessary because of the dorsal contact of the shaft with the calf and the arch support, which is obtained by arranging an arc at the inside of the foot, which rises substantially perpendicularly from the front edge of the heel and reaches its apex substantially at the level of the upper beginning of the heel part rounding and from which the opposite flank of the arc decends flatter towards the toe end of the foot part. Also unnecessary is an elevation of the shoe sole at the healthy foot because the orthopedic device positions the broken foot only about 1 to 2 cm higher.

Despite the obvious advantages of such known orthopedic devices, the fact remains that they must be built individually for each foot because the arch support is an integral part of the device. The device may be produced by thermoforming, different shaping tools being required for different sizes and for the left and right foot. This makes the manufacture expensive because the shaping tools are costly. In addition, these orthopedic devices require an undesirable store of different sizes and the left and right foot.

SUMMARY OF THE INVENTION

It is the primary object of this invention to provide an orthopedic device of the first-described type, which involves reduced manufacturing costs and less sorting.

In such an orthopedic device, the above and other objects are accomplished according to the invention if the bearing surface side facing the interior of the orthopedic device is flat and symmetrical with respect to a central longitudinal axis, the device comprises an arch support affixable to this bearing surface side, a portion of the arch support running along an outside of a foot capable of being supported by the arch support extending substantially horizontally, and a portion of the arch support running along an inside of the foot having a shape of a rising arc, a flank of the arc near the heel rising substantially perpendicularly from the bearing surface to an apex and extending from the apex to the foot part. The arch support has a top surface extending between the side-wall portion and the other side-wall portion and also extending between a heel and a toe end of the arch support. This top surface rises in height from the sidewall portion to the apex of the other side-wall portion and rises substantially perpendicularly from the continuous bearing surface in height from the heel end of the apex of the other side-wall portion and then descends in height toward the toe end. The top surface is spaced high enough from the continuous bearing surface to maintain the heel of the user freely floating above the continuous bearing surface.

The symmetrical arrangement of the bearing surface and thus of the entire orthopedic device means that it may be used for the right as wall an the left foot. In addition, only two basic sizes (one for children and the other one for adults) are needed, more customized sizing requiring only that a portion of the front of the device must be cut off. Therefore, at most two shaping tools are required for the manufacture of the shell of the orthopedic device. This substantially reduces the manufacturing casts.

To fit the orthopedic device to the injured foot, only a suitable arch support needs to be manufactured, which is then placed on the flat inside of the running surface and affixed thereto. The arch support may be affixed by an adhesive or a frictional connection, such as a Velcro connection. The latter has the advantage that the orthopedic device shell may be reused with another arch support, for example the arch support may be replaced during the healing process.

In one preferred embodiment, the arch support is made of a synthetic resin, such as a synthetic resin foam.

Preferably, the shaft, the heel part and the foot part are an integral synthetic resin part, and the shaft may be placed around the calf of the leg, and detachable closures may hold the shaft in position around the shin bone and the foot part in position at the foot. Advantageously, the detachable closures may also be Velcro devices, which make it possible to fit the device to the lower leg and the foot with some tolerances.

In another preferred embodiment, the orthopedic device further comprises a nonskid sole arranged below the heel part and the foot part to make walking more secure. To protect the toes, too, the foot part may comprise a cap enclosing the toes of the foot and a nonskid sole.

It is also useful to provide ankle bone protective pads arranged between the shaft and the heel part at both sides of the orthopedic device.

For purposes of control and suitable venting of the orthopedic device shell, the heel part may define an opening above the bearing surface.

BRIEF DESCRIPTION OF THE DRAWING

The above and other objects, advantages and features of the present invention will become apparent from the following detailed description of a presently preferred embodiment thereof, taken in conjunction with the accompanying somewhat schematic drawing wherein.

DETAILED DESCRIPTION OF THE PREFERRED EMBODIMENT

Figure 1:
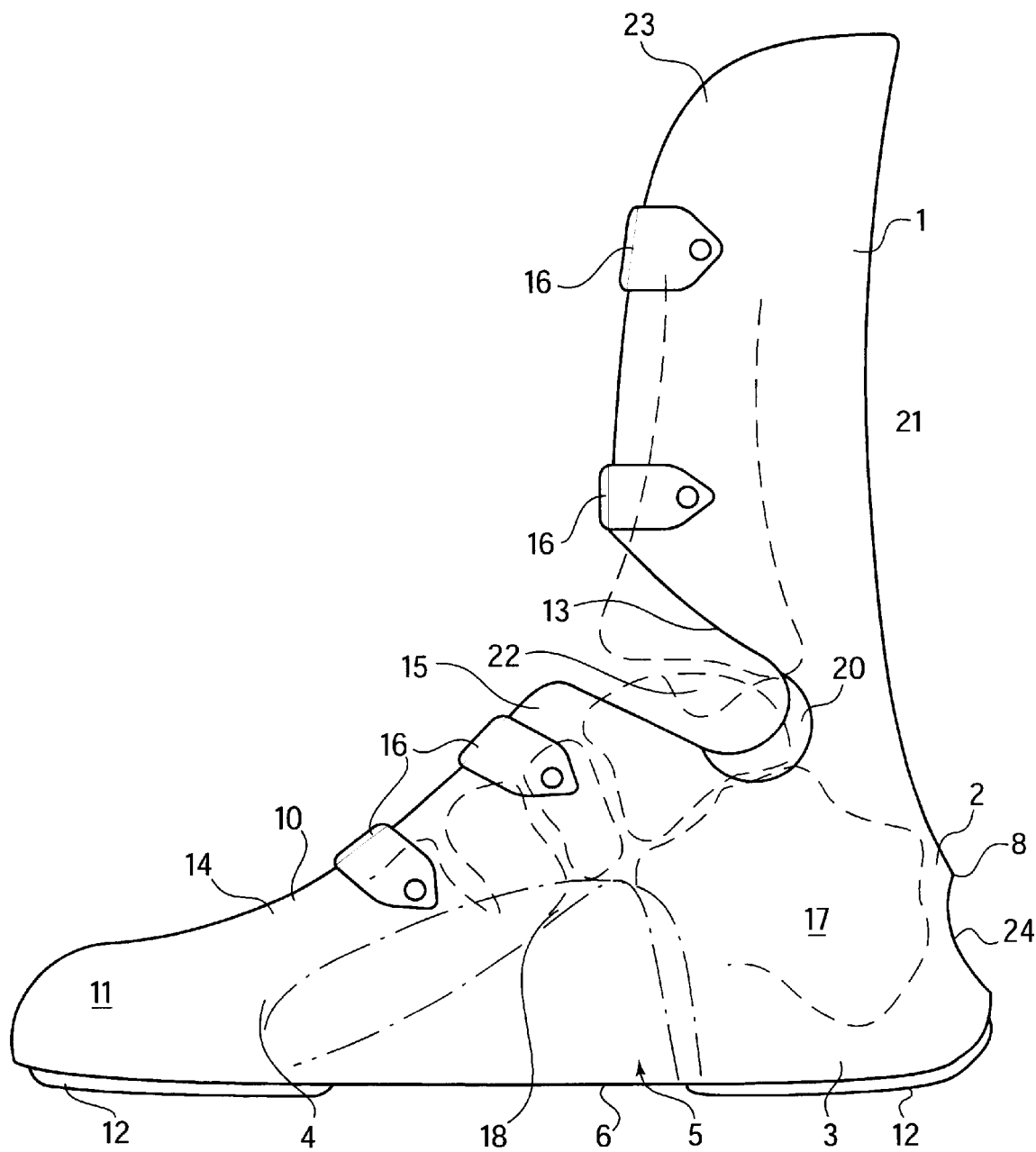
FIG. 1 is a side elevational view of an orthopedic device according to this invention, as seen from the inside of the foot.
Figure 2:
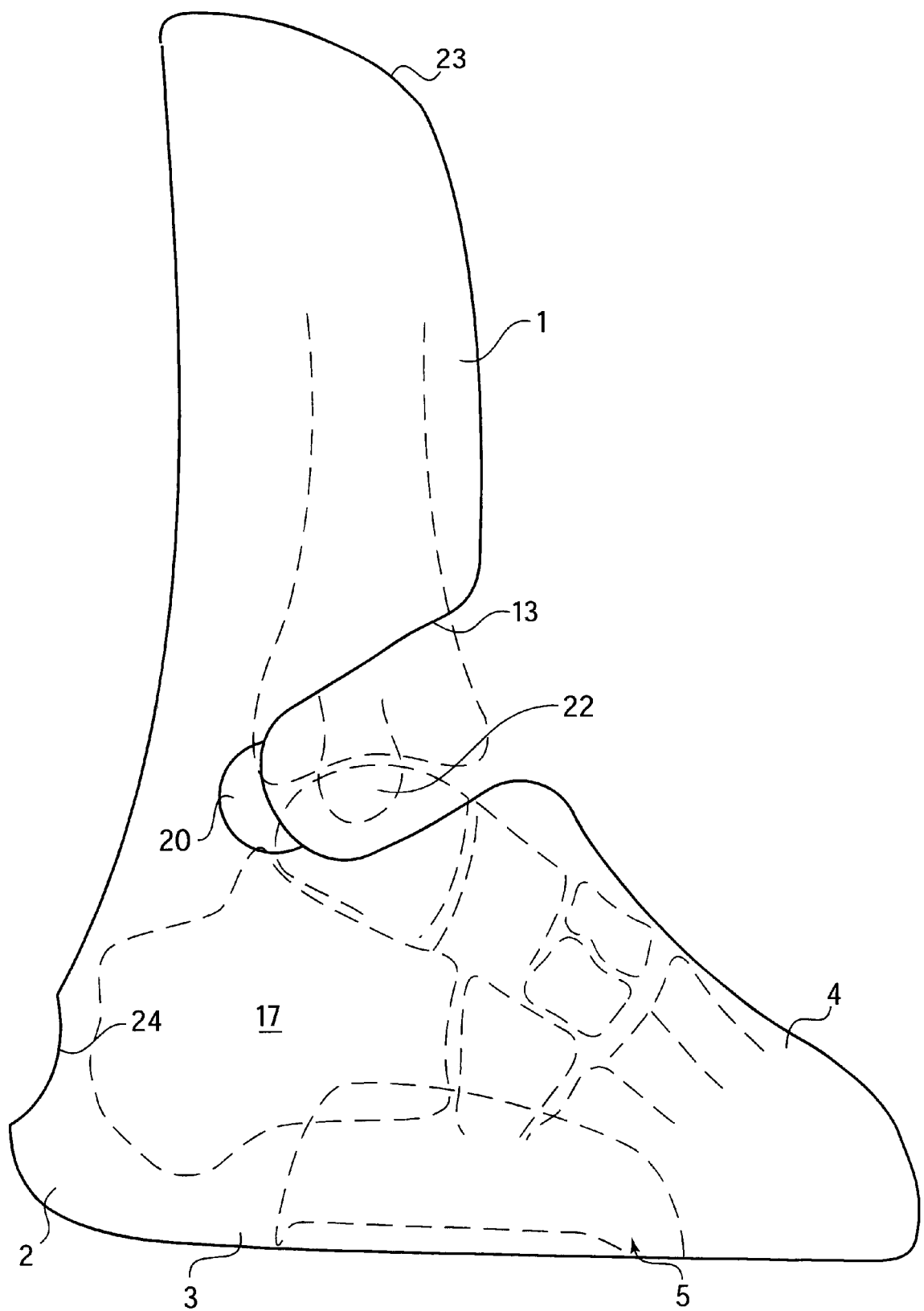
FIG. 2 is a like view, as seen from the outside of the foot.

Referring now to the drawing, FIGS. 1 and 2 show an orthopedic device, such as a heal relief device, which comprises shaft 1 capable of at least partially encircling at least a lower part of a leg, foot part 4 having a front end, and cup-shaped heel part 2 connecting the foot part to the shaft. Continuous bearing surface 6 is arranged between the front end of foot part 4 and heel part 2. The bearing surface constitutes a lower closure of the orthopedic device so that the device forms a shell receiving the foot and lower part of the leg, which are indicated in broken lines inside the orthopedic device shell. Bearing surface 6 has a side facing the interior of the orthopedic device shell, and according to this invention, this bearing surface inside is flat and symmetrical with respect to a central longitudinal axis. Arch support 5 is a separate shaped part affixable to the bearing surface inside between heel 3 and foot part 4.

Figure 3:
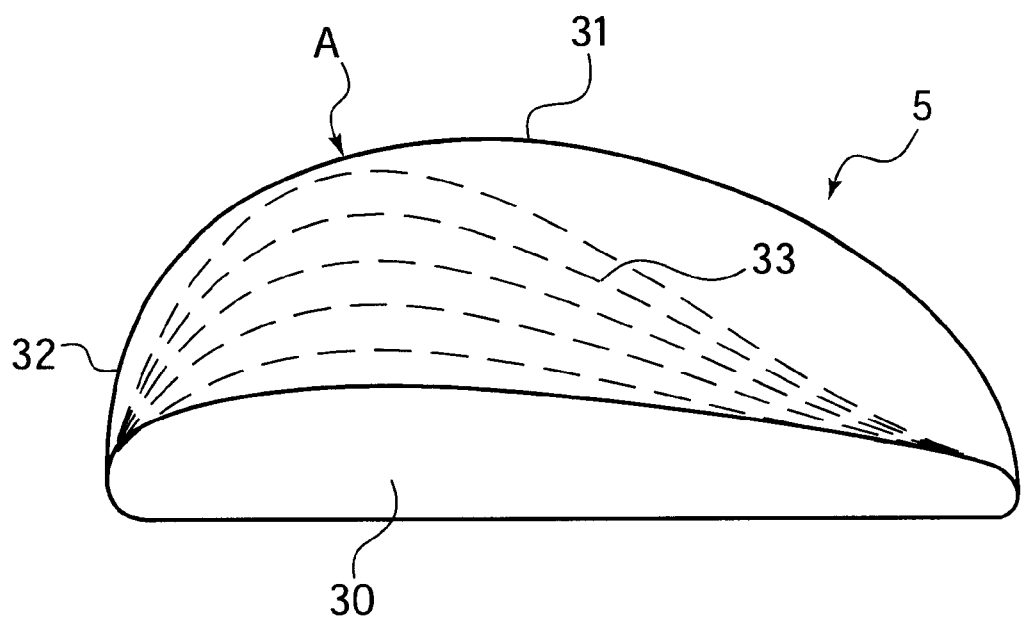
FIG. 3 is a side elevational view of the arch support, as seen from the inside of the foot.
Figure 4:
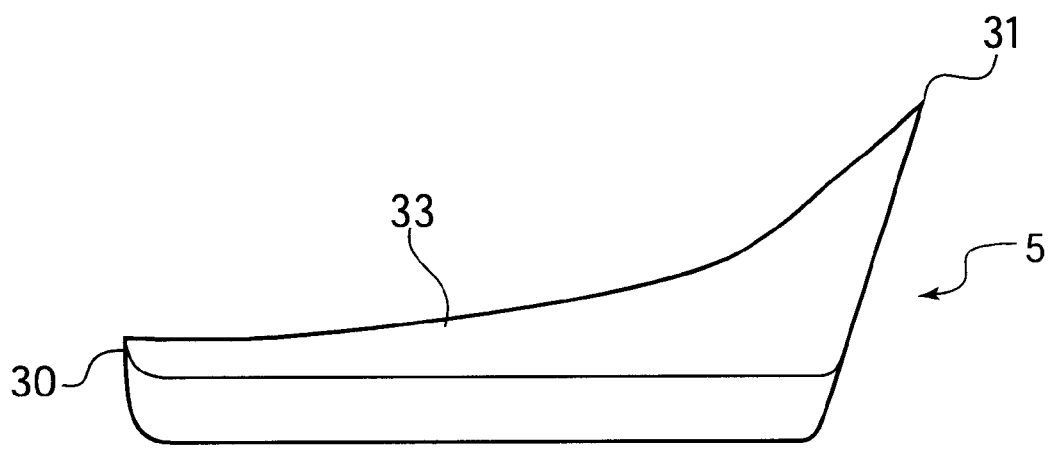
FIG. 4 is a front end view of the arch support.
Figure 5:
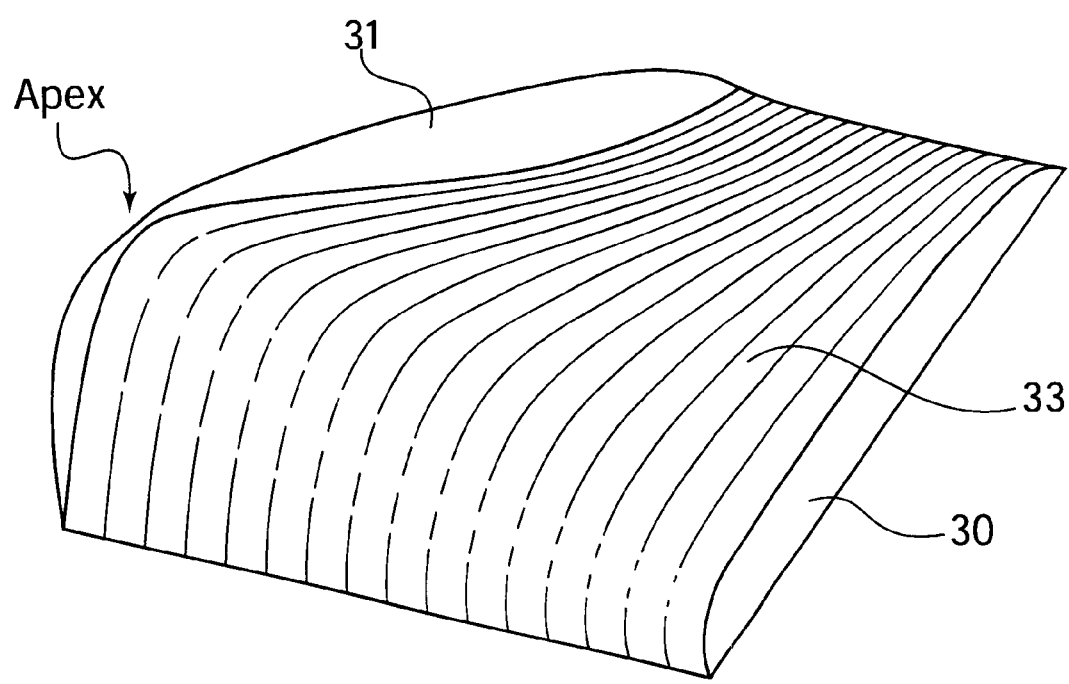
FIG. 5 is a perspective view of the arch support.

In accordance with the invention and as best shown in FIGS. 3–5, the arch support has two slightly inclined side wall portions 30, 31 of different height and a surface 33 between the side wall portions. Surface 33 is shaped to serve the orthopedic purpose of arch supports. The upper edge of lower side wall portion 30 running along an outside of a foot extends substantially horizontally, and the upper edge of higher side wall portion 31 of the arch support running along an inside of the foot has the shape of a rising arc, flank 32 of the arc near the heel rising substantially perpendicularly from the bearing surface to an apex A and extending from the apex A to the foot part in an acute angle, reaching at its end about the same height as the outside portion 30 of the arch support (see FIG. 3), The arch support may be affixed by an adhesive or a frictional connection, such as a Velcro closure.

The arch support say be made of a synthetic resin, preferably a foam.

In the preferred embodiment illustrated herein, shaft 1, heel part 2 and foot part 4 are an integral synthetic resin unit, which may be thermoformed, for instance by injection molding.

As shown in FIG 1, shaft 1 and foot part 4 comprise detachable Velcro closures 16 for holding the shaft and the foot part in position around the shin bone and the foot, respectively.

As also illustrated in FIG. 1, the orthopedic device further comprises a nonskid sole 12 arranged below the heel part and the foot part, the foot part comprising cap 12 enclosing the toes of the foot. Furthermore, ankle bone protective pads 20 are arranged between shaft 1 and heel part 2. Also, the heel part defines an opening 24 above bearing surface 6.

Shaft 1 reaches about the middle of the calf, and its upper edge 23 forms a convex arc bending forwardly towards the shin bone. At the level of the malleolus 22, the shaft edge is recessed close to the angle bones to form slot 13 so that the shaft exerts no pressure on the malleolus. Below slot 13, the edges of foot part 4 extend towards each other until they meet at edge 14 of toe cap 11.

In operation, the patient slides his foot into the open foot part 4 until the toes are positioned within cap 11. The two parts 14 and 15 of the foot part are then placed on the foot and are connected with each other by the two Velcro closures 16. The apex of arcuate side wall portion 31 of arch support 5 is now positioned in front of freely floating heel bone 17 in front of heel part 2 and, together with the more flatly descending flank of the arc, supports arch 18 as well as malleolus 22, as indicated in broken lines.

After the foot has thus been placed in the orthopedic device, the shaft is positioned around the lower leg and is closed at the shin bone by the two Velcro closures 16. The ankle bones are protected adjacent slot 13 by pads 20.

So protected during walking, the foot is able to act practically normally since the rounded heel part 2 will absorb the forces generated when the foot is put down and will transmit them to the calf portion 21 of shaft 1. Subsequently, arch support 5 will absorb the forces, and the heel bone remains relieved of any load during the entire movement.

The orthopedic device of the present invention looks and performs like a modern ski boot. Its interior may be vented by providing the opening 24 above heel 3 and, if desired, such an opening may also be provided in toe cap 11.

We claim:

1. An orthopedic device, such as a heel relief device, comprising
   (a) a shaft capable of at least partially encircling at least a lower part of a leg, (b) a foot part having a front end,
   (c) a cup-shaped heel part connecting the foot part to the shaft,
   (d) a continuous bearing surface extending along the foot part and the heel part, the bearing surface being adapted to support a foot, and the bearing surface constituting a lower closure of the orthopedic device and having a side facing the interior of the orthopedic device, said bearing surface side being flat and symmetrical with respect to a central longitudinal axis, and
   (e) an arch support affixable to said bearing surface side and extending only from the foot part up to a beginning of the heel part,
      (1) a side-wall portion of the arch support adapted to run along an outside of the foot and extending substantially linearly, and
      (2) another side-wall portion of the arch support adapted to run along an inside of the foot, said another side-wall portion having a shape of an arc, a flank of the arc near the heel part rising substantially perpendicularly from the bearing surface to an apex, and
      (3) a top surface of the arch support extending between the side-wall portion and the another side-wall portion and also extending between a heel and a toe end of the arch support, the top surface rising in height from the sidewall portion to the apex of the another side-wall portion and rising substantially perpendicularly from the continuous bearing surface in height from the heel end to the apex of the another side-wall portion and then descending in height toward the toe end, the top surface being spaced high enough from the continuous bearing surface to maintain the heel of the user freely floating above the continuous bearing surface.

2. The orthopedic device of claim 1, further comprising an adhesive for affixing the arch support to the bearing surface side.

3. The orthopedic device of claim 1, further comprising a frictional connection for affixing the arch support to the bearing surface side.

4. The orthopedic device of claim 1, wherein the arch support is made of a synthetic resin.

5. The orthopedic device of claim 4, wherein the synthetic resin is a foam.

6. The orthopedic device of claim 1, wherein the shaft, the heel part and the foot part are an integral synthetic resin part.

7. The orthopedic device of claim 1, wherein the shaft and the foot part comprise detachable closures for holding the shaft and the foot part in position around the shin bone and the foot, respectively.

8. The orthopedic device of claim 1, further comprising a nonskid sole arranged below the heel part and the foot part.

9. The orthopedic device of claim 1, wherein the foot part comprises a cap enclosing the toes of the foot and a nonskid sole.

10. The orthopedic device of claim 1, further comprising ankle bone protective pads arranged between the shaft and the heel part.

11. The orthopedic device of claim 1, wherein the heel part defines an opening above the bearing surface.

* * * * *